United States Patent [19]

Faupel et al.

[11] Patent Number: 5,678,547

[45] Date of Patent: Oct. 21, 1997

[54] METHOD AND APPARATUS FOR SCREENING OR SENSING BODILY CONDITIONS USING DC BIOPOTENTIALS

[75] Inventors: Mark L. Faupel, Conyers, Ga.; Charles Leonard Gordon, New York, N.Y.; John D. Stephens; Seth D. Nathanson, both of Alpharetta, Ga.; Kenneth E. Doe, Kent; Steven Erik Hagstrom, Bothell, both of Wash.

[73] Assignee: Biofield Corp., Roswell, Ga.

[21] Appl. No.: 429,138

[22] Filed: Apr. 26, 1995

Related U.S. Application Data

[63] Continuation-in-part of Ser. No. 213,021, Mar. 14, 1994, Pat. No. 5,427,098, which is a continuation-in-part of Ser. No. 859,170, Mar. 27, 1992, Pat. No. 5,320,101, which is a continuation-in-part of Ser. No. 579,970, Sep. 10, 1990, Pat. No. 5,099,844, which is a division of Ser. No. 288,572, Dec. 22, 1988, Pat. No. 4,955,383.

[51] Int. Cl.$^6$ .......................................... A61B 5/05
[52] U.S. Cl. .................. 128/653.1; 128/734; 128/639
[58] Field of Search ............................. 128/653.1, 733, 128/734, 639, 731; 364/413.02

[56] References Cited

U.S. PATENT DOCUMENTS

| | | |
|---|---|---|
| 4,328,809 | 5/1982 | Hirschowitz et al. |
| 4,407,300 | 10/1983 | Davis . |
| 4,416,288 | 11/1983 | Freeman . |
| 4,486,835 | 12/1984 | Bai et al. . |
| 4,557,271 | 12/1985 | Stoller et al. . |
| 4,557,273 | 12/1985 | Stoller et al. . |
| 4,617,939 | 10/1986 | Brown et al. ........................ 128/734 |
| 4,736,751 | 4/1988 | Gevins et al. ....................... 128/732 |
| 5,038,782 | 8/1991 | Gevins et al. ....................... 128/731 |
| 5,099,844 | 3/1992 | Faupel ............................... 128/653.1 |
| 5,099,856 | 3/1992 | Killion et al. ....................... 128/731 |
| 5,263,487 | 11/1993 | Sakamoto et al. ................... 128/731 |
| 5,368,041 | 11/1994 | Shambroom ......................... 128/731 |
| 5,409,011 | 4/1995 | Alexeev et al. ..................... 128/731 |
| 5,479,934 | 1/1996 | Imran ................................ 128/731 |
| 5,529,072 | 6/1996 | Sramek .............................. 128/734 |
| 5,533,522 | 7/1996 | Feng ................................. 128/731 |

*Primary Examiner*—Brian L. Casler
*Attorney, Agent, or Firm*—Sixbey, Friedman, Leedom & Ferguson; Daniel W. Sixbey

[57] ABSTRACT

A method and apparatus for screening or sensing disease states, injury sites or bodily conditions in a human or animal subject by separately detecting the DC biopotential of the electromagnetic field at a plurality of test points in a test area. The DC biopotentials are converted by analog to digital converters connected to DC biopotential test sensors at the test points into digital test signals, and the DC biopotential test sensors and analog to digital converters form a biopotential sensing section which is separate from a processing section that receives and processes the digital test signals. Signals between the processing section and the biopotential sensing section are transmitted by a transmission network which electrically isolates the two sections. The conversions performed by the analog to digital converters are synchronized with the AC line frequency of the apparatus power supply, and the digital test signals are filtered in the processing section by digital filters, each of which is dedicated to an individual DC biopotential test sensor.

23 Claims, 3 Drawing Sheets

|| 5,678,547 ||

METHOD AND APPARATUS FOR SCREENING OR SENSING BODILY CONDITIONS USING DC BIOPOTENTIALS

This application is a continuation-in-part application of Ser. No. 08/213,021 filed Mar. 14, 1994 now U.S. Pat. No. 5,427,098, which is a continuation-in-part of Ser. No. 07/859,170 filed Mar. 27, 1992, now U.S. Pat. No. 5,320, 101, which is a continuation-in-part application of Ser. No. 07/579,970, filed Sep. 10, 1990, now U.S. Pat. No. 5,099, 844, which is a divisional application of Ser. No. 07/288,572 filed Dec. 22, 1988, now U.S. Pat. No. 4,995,383.

TECHNICAL FIELD

The present invention relates generally to a method and apparatus for screening or sensing disease states, injury sites or bodily conditions in a living organism by detecting the DC biopotential of the electromagnetic field present between a reference and a plurality of test points on the living organism to measure the gradient of electrical activity which occurs as a function of biological activity.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et al. deals with a device and method for detecting the potential level of the electromagnetic field present between a reference point and a test point on a living organism. In Hirschowitz et al., a reference electrode and a test electrode provide DC signals indicative of the potential level of the electromagnetic field measured between the reference point and the test point. These signals are provided to an analog-to-digital converter which generates a digital signal as a function thereof, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. Nos. 4,416,288 to Freeman and 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnostic inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These and other effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). The tumor may not respond significantly to growth factors, while the growth factors and the enzymes produced may significantly affect the normal cells surrounding the tumor. Once this fact is recognized, it follows that important electrical indications of disease are going to be seen in the relative voltages recorded from a number of sites at and near a diseased area, and not, as previously assumed, on the direction (positive vs. negative) of polarity.

The accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial amount of noise which makes accurate analysis difficult. Also, biological systems are notorious for their complexity, nonlinearity and nonpredictability, and wide variations from the norm are not uncommon. For example, DC biopotential signals tend to drift over time, so that if signals are not sensed and analyzed with some rapidity, signal errors due to drift occur. However, the low pass filters used to remove undesirable high frequency AC components from sensed DC biopotentials require stabilization periods between signal measurements which tend to unduly prolong the test period during which measurements are taken.

DISCLOSURE OF THE INVENTION

It is a primary object of the present invention to provide a novel and improved apparatus for disease, injury or bodily function screening or sensing which employs the measurement and analysis of DC biopotentials taken from the area of a site on a living organism to monitor the efficacy of a treatment for the disease, injury, or bodily function.

Another object of the present invention is to provide a novel and improved apparatus for disease, trauma or other injury or bodily condition screening or sensing wherein a plurality of DC biopotentials from different areas of a site on a living organism are rapidly measured and processed during a short test period to provide information indicative of a particular condition.

A further object of the present invention is to provide a novel and improved apparatus for disease, injury or bodily condition screening or sensing wherein DC biopotentials received on separate channels from a plurality of separate sites at and near a suspected area of disease, injury or condition change on a living organism are integrated and digitized. The digitized signals from each channel are then individually filtered by a dedicated digital filter and averaged. A maximum potential differential is then obtained from the averages of digitized, filtered biopotential values from all channels to obtain an indication of a disease, injury or other bodily condition.

Yet a further object of the present invention is to provide a novel and improved apparatus for disease, injury or condition screening or sensing wherein DC biopotentials are received from a plurality of measuring electrodes located on the skin of a subject in the area of a suspected disease, injury or condition change site. To protect the subject from possible electric shock, the higher voltage AC portions of the apparatus are electrically isolated from the lower voltage DC portions which are in contact with the subject.

A still further object of the present invention is to provide a novel and improved method and apparatus for disease, injury or bodily condition screening or sensing wherein analog biopotentials are separately received from a plurality of measuring electrodes located on the skin of a subject in the area of the site of a suspected condition. These analog potentials are digitized, and the digitized values are reviewed prior to further mathematical processing to eliminate any digital values which correspond to sensed DC biopotentials that are not within a predetermined millivolt range.

Yet a further object of the present invention is to provide a novel and improved method and apparatus for bodily condition screening or sensing wherein a multiplicity of DC biopotentials are received from each of a plurality of measuring electrodes and digitized. The analog to digital conversion of the DC biopotentials is synchronized with the AC line frequency to minimize AC power supply induced noise.

DETAILED DESCRIPTION OF THE INVENTION

Figure 1:
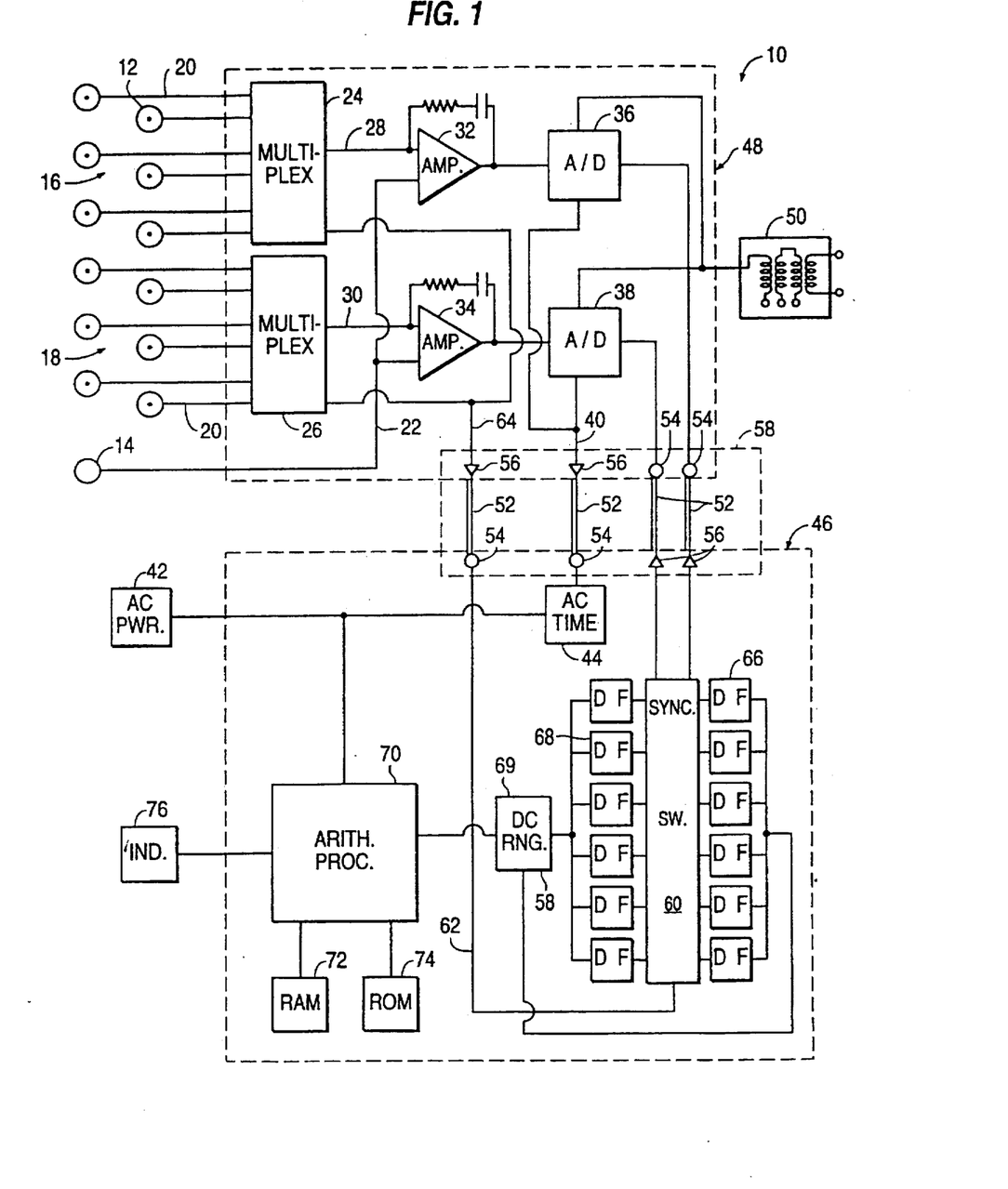
FIG. 1 is a block diagram of the apparatus of the present invention.

FIG. 1 discloses a basic block diagram of the apparatus of the present invention indicated generally at 10 for performing a discriminant analysis to obtain a differential signal indicative of the presence, absence, or state of a condition at a test site on a human or animal subject. To accomplish this, a plurality of DC biopotential sensors for sensing DC biopotentials, such as sensing electrodes 12 and at least one reference electrode 14 are used to provide analog outputs indicative of DC biopotentials.

The method of this invention contemplates the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. The aim is to measure the areas of electrical activity which occurs as a function of the underlying biological activity of the organ system. The number of electrodes 12 used in the measurement will also be a function of the specific application.

In FIG. 1 for purposes of illustration, two electrode arrays 16 and 18 are shown with each array consisting of six electrodes 12 providing six separate output channels for each array. In actual practice, each array can contain more electrodes and more than two arrays can be employed.

The electrodes 12 of the electrode arrays 16 and 18 should be mounted in a manner which permits the electrodes to be accurately positioned against the curved surface of the skin of a subject in the area of a test site while still maintaining uniform spacing and the position of the electrodes in a predetermined pattern. The electrodes 12 and reference electrode 14 must all be of a type suitable for detecting DC biopotentials indicative of the potential level of the electromagnetic field present in a living organism. These electrodes should be of a type which do not cause a substantial battery effect between the organism under test and the electrodes and must have a very low DC offset potential.

The device 10 is a multi-channel device having electrode leads 20 extending separately from the electrodes 12 in each array and an electrode lead 22 extending from the reference electrode 14. Each electrode 12 in combination with the reference electrode 14 forms a separate data channel which transmits a plurality of analog signals indicative of the DC biopotentials at a specific site in a test area. The electrode leads 20 from the array 16 are connected to a solid state multiplexor 24 such as a Harris Semiconductor Model HI-546-5, while the electrode leads from the electrode array 18 are connected to a second solid state multiplexor 26. Each electrode array connected to the device 10 provides a plurality of outputs to a multiplexor connected to the array, and this multiplexor switches between the electrode leads 20 during a test period to connect the analog signals on each lead sequentially to a multiplexor output such as the output lines 28 and 30 to create a time division multiplexed output. By dividing the electrodes 12 into a plurality of arrays and by providing a high speed solid state multiplexor for each array, it is possible to repeatedly sample biopotentials from a large number of electrodes during a test period of minimal duration.

In the past, a low analog pass filter has been used to filter the signals from the electrodes 12. The filter operated to remove undesirable high frequency AC components which appear on the slowly varying DC voltage signal outputs provided by each of the electrodes as a result of the electromagnetic field measurement. To be effective, the cutoff frequency of such filters had to be very low, normally within a range of from 1 to 27 Hertz, and the filter required a long stabilization period each time a new signal of a different amplitude was received. The lower the cutoff frequency of the filter, the longer the stabilization time required, and thus the delay caused by filter operation significantly reduced the number of channels which could be sampled during a reasonable test period. Also, as slow filter response increased the time between samples, DC signal drift tended to affect the accuracy of samples taken from each individual electrode over the test period.

To minimize the filter stabilization period, a separate low pass analog filter could be provided for each channel, so that each individual filter would theoretically not receive analog signals of significantly different amplitudes during a test period and thus significant filter stabilization periods would not be required. Where a large number of electrodes and channels are present, this solution would require an inordinate number of filters, and since no two channels would pass through the same filter, the likelihood of one or more filters operating differently from the remaining filters to cause an error is increased.

In the device 10 of the present invention, the analog signals on the outputs from each multiplexor are passed through separate relatively higher frequency low pass filter amplifiers, such as the filter amplifiers 32 and 34. These filter amplifiers have a relatively high cutoff frequency of 40 Hertz or more, and thus require a short stabilization period with analog signals of the amplitude provided on the output lines 28 and 30 to the filters.

The analog output signals from the filter amplifier 32 connected to the multiplexor for the electrode array 16 are directed to an analog to digital converter 36, while the analog output signals from the filter amplifier 34 for the electrode array 18 are connected to an analog to digital converter 38. The analog to digital converters operate to convert the input analog signals to output digital signals which are a function of the analog inputs.

Figure 2:
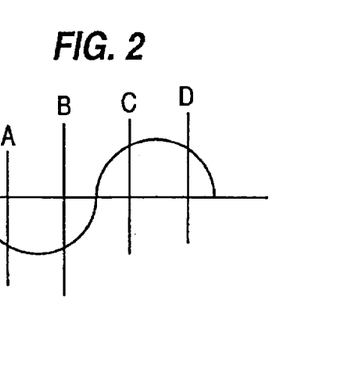
FIG. 2 illustrates the manner in which the analog to digital converters of FIG. 1 are synchronized to the AC line frequency.

The analog to digital converters 36 and 38 operate in response to timing signals provided on a timing line 40 which synchronize the conversions with the line frequency of the AC power line 42 for the device 10. The AC line frequency is a large source of noise which adversely affects the biopotential signals sensed by the device, and this line frequency noise is minimized by synchronizing the analog to digital conversions with the line frequency. To accomplish this, an AC timer section 44 in a central processor unit 46 such as a Motorola Model 68332, senses the AC power line frequency and provides four timing pulses on the timing line 40 at equal positions A, B, C and D on the sine wave for the AC line cycle as shown in FIG. 2. The timing pulses occur equal distances from the peak or 90° point of each half cycle and on opposite sides thereof. Ideally, these timing pulses occur at points on the half cycle which are 90° from the peak point. Thus, a timing pulse is provided at an equal position on the rise and fall curve of each half cycle, causing a conversion to occur in response to each timing pulse. Noise generated during the rise portion of the half cycle tends to be cancelled by noise generated during the fall portion.

The multiplexors 24 and 26, the filter amplifiers 32 and 34 and the analog to digital converters 36 and 38 form an isolation section 48 which is electrically connected to a subject by means of the electrode arrays 16 and 18. This isolation section is provided with a lower power dedicated power supply 50 which does not provide power sufficient to cause injury to a subject. The power supply 50 receives AC power from the AC powerline 42 and includes a dual isolation circuit including two transformers between the AC powerline and the isolation section which provide a dual barrier to the AC powerline. The power supply 50 converts the input AC to a low voltage DC which powers the isolation section 48. The isolation section is electrically isolated from the central processor unit 46 which is connected to the AC powerline 42. To achieve this electrical isolation, all signals between the isolation section and the central processor unit may be conducted over optical cables 52 as optical signals. Thus, the timing signals from the AC timer section 44 are converted to light pulses by a conversion unit 54, such as a light emitting diode, transmitted over an optical cable 52 and reconverted to electrical pulses by a reconversion unit 56. Similarly, the electrical digital outputs from the analog to digital converters 36 and 38 are converted to light pulses and transmitted to the central processor 46 where they are reconverted into electrical digital signals. Alternatively, an optoisolator chip shown in broken lines at 58 such as Hewlett Packard Model CNW136 may replace the optical cables 52, conversion units 54 and reconversion units 56 to convert the electrical signals to optical signals and to accomplish the reconversion. The electrical digital signals from either the reconversion unit 56 or the optoisolator chip 58 are directed to a synchronous switching or de-multiplexer 60.

The de-multiplexer 60 is synchronized with the multiplexors 24 and 26 and provides timing signals on a line 62 which are transmitted as optical signals to the isolation section 48 where they are reconverted to electrical timing signals which are sent over a line 64 to the multiplexors. Digital filter arrays 66 and 68 in the software for the central processing unit include a dedicated digital filter such as two-pole, Infinite Impulse Response (IIR) filter, with a Butterworth response, for each electrode channel in the electrode arrays 16 and 18 respectively. Thus, as the multiplexors 24 and 26 are simultaneously transmitting analog signals from a selected electrode channel in the electrode arrays 16 and 18, the digital signals indicative of these analog signals are being directed by the de-multiplexor to the digital filters in the arrays 66 and 68 which are dedicated to those channels. When the multiplexors switch channels, the de-multiplexor switches to corresponding digital filters.

Filtered digital data from the digital filter arrays 66 and 68 are analyzed by a DC range sensing section 69 of the central processing unit (that is in fact formed by a software program) which is programmed to sense the magnitude of the DC biopotential signals represented by the filtered digital signals. Digital signals indicative of DC signals within a predetermined range of millivolts (for example −30 to +100 millivolts) are accepted while signals outside this millivolt range are rejected as spurious. The accepted signals are directed to processing section 70 of the central processor unit 46 having a RAM memory 72 and a ROM memory 74. This data is stored in memory and is processed by the processing section in accordance with a stored program to perform the condition screening or sensing functions of the present invention. The output from the processing section is connected to control the display on an indicator unit 76.

It should be understood that for clarity of description, sections of the central processor unit 46 have been illustrated as operative blocks, but these sections may constitute software controlled functions.

The operation of the apparatus 10 will be clearly understood from a brief consideration of the broad method steps of the invention which the device is intended to perform. The electrode arrays 16 and 18 are positioned over various diverse areas of a test site, and the reference electrode 14 is then brought into contact with the skin of the subject in spaced relationship to the electrode arrays. This reference electrode might, for example, be brought into contact with a hand or sub-xyphoid area of the subject. The electromagnetic field between the reference electrode and each of the electrodes 12 is measured, converted to a digital signal and stored for processing by the processing section 70. The program control for the central processor unit causes a plurality of these measurements to be taken over a period of time, and the measurements on all channels are taken repetitively during a predetermined measurement time or test period. Sequential measurements between the reference electrode and one of the electrodes 12 in each array 16 and 18 are taken until each channel is sampled, and then the sequential measurement is repeated throughout the duration of the predetermined test period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the processing section 70 at the end of the test period. For the duration of a single test period, for example, from twelve measurement channels, the processing section will obtain twelve average signals indicative of the average electromagnetic field for the test period between the reference electrode 14 and each of the electrodes 12 in the electrode arrays 16 and 18. Of course, more reference electrodes can be used, although only one reference electrode has been shown for purposes of illustration.

Having once obtained an average signal level indication for each channel, the results of the measurements taken at multiple sites are analyzed mathematically to determine the relationships between the average signal values obtained. It has been found that the result of such an analysis is that a subset of relationships can be obtained which are indicative of the presence of more serious disease, injury or other condition, while a different subset might be obtained which will be indicative of the absence of such conditions.

One of the most important relationship to be obtained is the maximum voltage differential (MVD), which is defined as the minimum average voltage value obtained during the test period subtracted from the maximum average voltage value obtained for the same period where two or more electrodes are recording DC potentials from a test site. Thus, for each predetermined test period, the lowest average voltage level indication obtained on any of the channels is subtracted from the highest average voltage level indication obtained on any of the channels to obtain an MVD voltage level. If this MVD voltage level is above or below a desired level >x, then a disease condition, such as a malignancy, injury or other condition could be indicated. Similarly, if the average taken over the measurement period from one channel is an abnormally low value <y, the presence of this abnormally low individual electrode reading (IER) could be indicative of a disease condition, injury or other condition. These primary indicators may be further analyzed to reduce the number of false positive diagnoses which may be falsely identified on the basis of high MVD or low IER readings.

Figure 3:
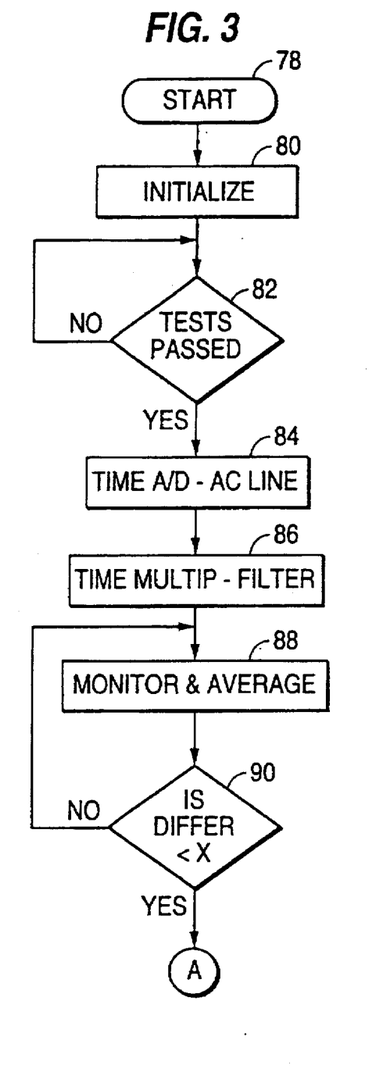
FIGS. 3 and 4 are flow diagrams illustrating the operation of the central processor of FIG. 1 to obtain a maximum voltage differential.
Figure 4:
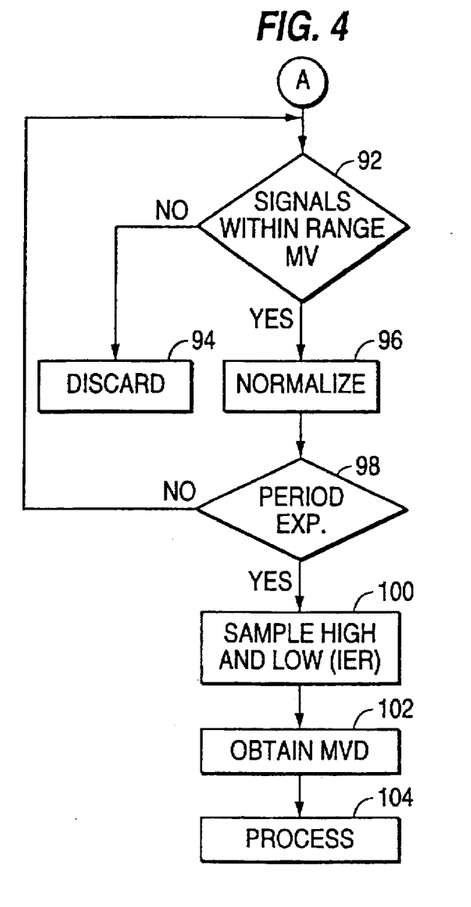

The general overall operation of the central processing unit 46 will best be understood with reference to the flow diagrams of FIGS. 3 and 4. The operation of the unit 10 is started by a suitable start switch as indicated at 78 to energize the central processing unit 46, and this triggers an initiate state 80. In the initiate state, the various components of the device 10 are automatically brought to an operating mode, with for example, the indicator 76 being activated while various control registers for the central processing unit are reset to a desired state.

Subsequently, a test period is initiated at 82 wherein the various components of the system are tested for proper operability. During this test period, the electrode arrays 16 and 18 may also be tested to make certain that electrodes are being used which accurately measure DC biopotentials.

If all system components test out properly during the system test period, then timing of the analog to digital converters in accordance with the AC line frequency begins at 84 and the timing of the multiplexors and de-multiplexors begins at 86. With the analog to digital converters, multiplexors, de-multiplexors and digital filters in operation, it is now possible to monitor the biopotential signals from a test area during a monitoring period begun at 88. During this monitoring period, conditions in the test area contacted by the electrode arrays 16 and 18 are stabilized so that subsequent reliable measurements of DC biopotentials can be obtained. Since the stabilization period for different subjects varies, some unknown time period must lapse before reliable measurements of DC biopotentials are obtained. Thus, at 88, a predetermined monitoring period is initiated, and the signals on all channels are monitored and averaged. Then, at the end of the initial monitoring period, the individual signals are compared to the average to obtain a value indicative of the relationship therebetween, and if this relationship value is greater than a predetermined value x, then sufficient signal stabilization has not occurred during the monitoring period and a new monitoring period is initiated. Conversely, if the relationship values obtained are less than the predetermined value x, then the monitoring period is terminated and a test period is initiated. Alternatively, the monitoring period can be an extended time period, for example, ten minutes, which is used for all patients and is sufficient to insure signal stabilization.

With reference to FIG. 4, during the test period the digitized signals received from the various sequenced channels are monitored at 92 to determine whether or not each biopotential represented by the signals is within a predetermined range of millivolts. Digitized values indicative of DC signals outside this range are discarded at 94 and the remaining signals are used to provide an average or normalized value for each channel at 96. The average value for each channel is obtained by summing the values obtained for that channel during the test period and dividing the sum by the number of measurements taken. Then, at 98, the central processor unit determines whether the test period has expired and the desired number of measurements have been taken, and if not, the collection of measurement samples or values continues.

Once the measurement or test period has expired, a final average value for each channel derived from the measurements taken during the span of the test period is available, and from these average values, the highest and lowest average value obtained within or between channels during the test period is sampled at 100. The lowest average channel value is subtracted from the highest average channel value at 102 to obtain a maximum voltage differential value. This maximum voltage differential value is then processed at 104 to indicate the presence or absence of a disease, injury, or other bodily condition, and during processing, can be compared with previously obtained differential values to determine the efficacy of treatment or the profess of a disease, injury or other bodily condition. The differential value may also be used to indicate the occurrence of a number of normal bodily functions such as ovulation, and normal or abnormal labor conditions.

In accordance with the present invention, the central processing unit 46 may be programmed to obtain the maximum voltage differential value by an alternate method. As will be noted from FIG. 1, signals from a first electrode pair consisting of a reference electrode, such as the electrode 14 and a sensing electrode in the array 16 are being obtained simultaneously with signals from a second electrode pair consisting of a reference electrode and a sensing electrode in the array 18. During each test period, multiple measurements are taken simultaneously from an electrode pair in the array 16 and an electrode pair in the array 18, and then the multiplexors 24 and 26 select a new electrode pair in each array and multiple measurements are taken from the two new electrode pairs. This continues until plural measurements are received from a plurality (X number) of first and second electrode pairs and the test period ends. Rather than averaging all signals from each individual electrode pair at the end of the test period, it is possible to compare each signal taken from a first electrode pair in the array 16 with each signal taken from a second electrode pair in the array 18 and to obtain and store a differential between each of these signals. Thus, if 150 signals from each first and second electrode pair are taken during a test period, there will be 150 differentials stored from each first and second electrode pair in the arrays 16 and 18 before the multiplexor sequentially switches to another first and second electrode pair. These 150 differentials are then averaged to obtain a single average differential for each first and second electrode pair combination, and this differential is stored for comparison with the remaining differentials obtained from measurements by the arrays 16 and 18 during the test period. At the end of the test period, there will be X number of stored differential averages, and a high and low of these can be chosen with the low being subtracted from the high to obtain a final maximum voltage differential. Normally, the highest and lowest average differential for the test period would be chosen to obtain the final maximum voltage differential.

Figure 5:
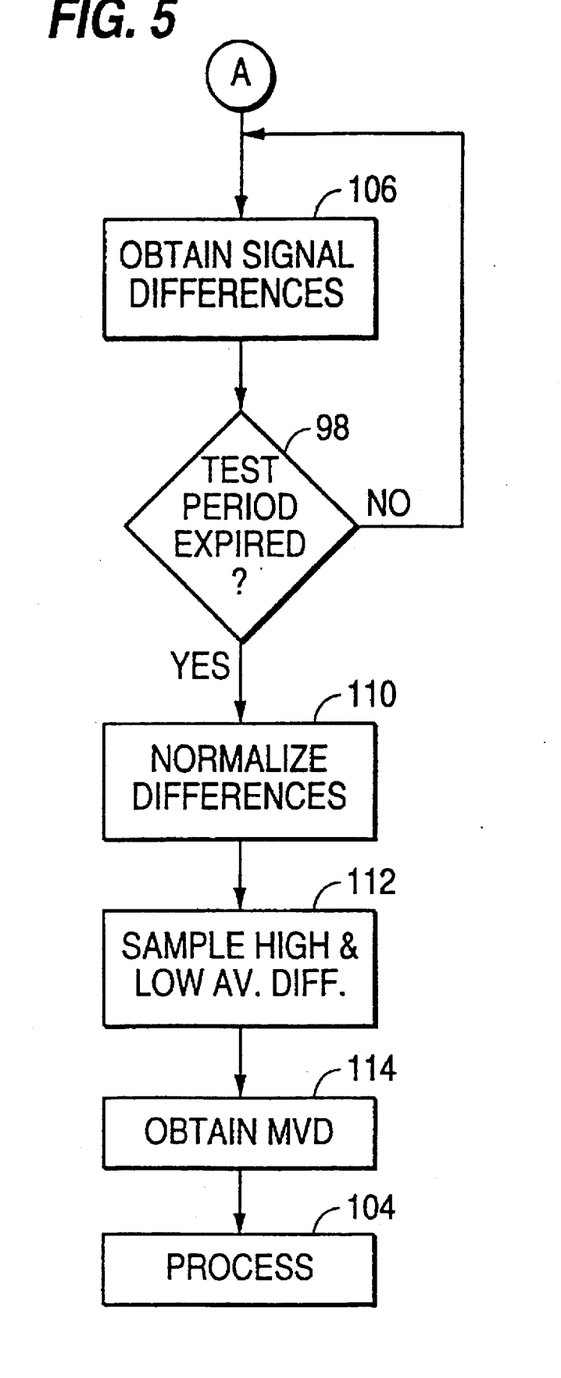
FIG. 5 is a flow diagram illustrating the operation of the central processor of FIG. 1 to obtain a maximum voltage differential by a second method.

To achieve this alternate method of obtaining a maximum voltage differential, the processing unit 46 is programmed to replace the flow diagram of FIG. 4 with the flow diagram of FIG. 5. In FIG. 5, two digitized signals as they are generated by the arrays 16 and 18 are compared at 106 to obtain a difference value between the two signals each time the signals from a specific electrode pair in each of the two arrays are obtained. When the central processing unit determines that the test period has expired at 98, the multiple difference values from these two specific electrode pairs are normalized or averaged at 110. Then the average differential values for all electrode pairs in both arrays which operate during the test period are sampled at 112 and a high and low differential value are identified. Generally, the differential values which are identified at 112 are the highest average differential and the lowest average differential taken during the test period, and at 114 the low is subtracted from the high to obtain a final maximum voltage differential value. This maximum voltage differential value is processed at 104 in the manner previously described. For example, this final maximum differential value can be compared at 104 to a predetermined reference value, and the relationship between the two used to determine whether or not a disease, injury, or other bodily condition is present.

It is quite possible that, for breast cancer detection, the array 16 might be placed on one breast of the subject and the array 18 could be placed on an opposite breast. Then, differential values between the breasts might be obtained and compared using either of the two of the methods previously described. For example, the signals from each channel from the left breast can be averaged at the end of the test period and the signals for the individual channels from the right breast may be averaged at the end of the test period, and these average values could then be used to obtain a maximum differential value for each breast. The maximum differential value obtained from the right breast might then be compared to a maximum differential value obtained for the left breast, and the difference might be used to obtain an indication. Obviously, the differential value from the right breast and the left breast may be acquired using the method disclosed in FIG. 5, and alternatively, a differential value might be obtained by taking the highest and lowest average from all of the average values obtained from both the left and right breasts and then subtracting the lowest from the highest value. Any final differential values so obtained may be analyzed to provide indications as to the presence or absence of various conditions.

Using the apparatus 10 of the present invention, it is possible to program the central processor unit 46 to use vector or other interpolative methods to model or simulate values of the biopotentials from points on the body not directly measured by the electrode arrays 16 and 18. The electrodes in each array are mounted on a flexible support sheet or a harness which maintains a preset spacing between electrodes, and for most applications, the electrodes are mounted in a pattern at known positions or measuring points. Using a vector summing method, point source voltage potentials measured by each electrode in an array are used as the basis for inferring voltages at points in the vicinity of the electrodes which are not directly measured by the electrode array. Each interpolated point is the sum of the average potentials contributed by each measured point during a test period relative to the vector distance from the interpolated point to each measured point. This results in a map of voltages (or isopotentials) which can be used to generate an image and can be displayed either as contours or spectral shading. In the former case, isopotential contours can be displayed as a series of discrete curves, the density of which are indicative of pronounced potential differences. In the latter case, color or grey scale shading which corresponds to the measured and interpolated voltages can be used to highlight areas of hyperpolarization and depolarization. Mathematical transformations of the actual voltages may provide additional information. For example, interpolated voltages can be transformed to differentials, allowing spectral shading to indicate electropotential differentials in areas of tissue.

Interpolation can occur in either two or three dimensions. In two dimensional mapping, x and y coordinates are spatial and represent the surface of the structure or tissue in question. The measured and interpolated voltages are then displayed as a third variable using contours or spectral shading as described above. In three dimensional mapping, a third spatial variable (z) is added, and interpolated voltages are mapped not only on the surface of the structure or tissue, but also as values mapped internally to the structure or tissue in question.

In both two and three dimensional mapping, precise distance and spatial information regarding the actual measurement points enhances resolution. If this information is available for three dimensional imaging, the resultant map of interpolated values could be displayed as a series of two dimensional slices. In either case, display would occur via a VDT or computer generated hard copy.

Industrial Applicability

The method and apparatus of the present invention may be employed to effectively indicate the state of disease, injury or other bodily conditions by using DC biopotentials taken from a plurality of different areas of a test site. DC signal drift and AC line frequency noise are minimized by taking measurements during a test period of minimal duration, using a digital filter for each measurement channel, and synchronizing analog to digital conversions to the AC line frequency. In use, the patient is protected from electrical shock by electrically isolating the biopotential measuring section of the apparatus from the processing section.

We claim:

1. An apparatus for sensing a condition at a test site on a human or animal subject by detecting DC biopotentials during a test period which are a function of the electromagnetic field present in the subject at the test site, said apparatus being powered by an AC power supply having an AC line frequency and comprising:

at least one DC biopotential reference sensor for contacting the subject at a reference location, a plurality of DC biopotential test sensors for contacting the subject at spaced locations at the test site, each said test sensor operating with a reference sensor to detect DC biopotentials which are present in the area of said test site and to provide DC test potentials as a function thereof, an analog to digital converter operably connected to said test sensors for receiving said DC test potentials and for converting said analog DC test potentials to digital test signals, a timing circuit for sensing said AC line frequency and controlling said analog to digital converter to synchronize the conversion operations of said analog to digital converter with said AC line frequency.

2. The apparatus of claim 1 wherein said timing circuit causes said analog to digital converter to provide two conversion operations for each half cycle of AC line frequency.

3. The apparatus of claim 2 wherein said timing circuit causes said analog to digital converter to provide a conversion operation at points on each half cycle of AC line frequency which are substantially equidistant from a peak 90 degree point of such half cycle and are on opposite sides of said peak point.

4. The apparatus of claim 1 which includes a digital processor connected to receive said digital test signals from said analog to digital converter, said processor operating during a test period to sample a plurality of digital test signals which are a function of a plurality of DC test potentials from each test sensor and to identify potential relationships therebetween.

5. The apparatus of claim 4 wherein said processor provides control signals to control a sampling of DC test potentials during a test period, said processor including said timing circuit for providing conversion timing signals to control the conversion operations of said analog to digital converter.

6. An apparatus for sensing a condition at a test site on a human or animal subject by detecting DC biopotentials during a test period at the test site, said apparatus being powered by an AC power supply having an AC line frequency and comprising:

a biopotential sensing section including at least one DC biopotential reference sensor for contacting the subject at a reference location, a plurality of DC biopotential test sensors for contacting the subject at spaced locations at the test site, each said test sensor operating with a reference sensor to detect DC biopotentials and to provide DC test potentials as a function thereof, and an analog to digital converter connected to said test sensors for receiving said DC test potentials and for performing conversion operations for converting said DC test potentials to digital test signals, a processing section connected to said AC power supply and including a digital processor operative during a test period to sample digital test signals which are a function of a plurality of DC test potentials from each test sensor and to identify potential relationships therebetween, said processor operating to provide control signals to said biopotential sensing section during said test period, the processor sensing said AC line frequency and providing control signals to said analog to digital converter to synchronize the conversion operations of said analog to digital converter with said AC line frequency, and an isolation circuit connected between said biopotential sensing section and said processing section to transmit control signals to said biopotential sensing section and digital test signals to said processing section, said isolation circuit operating to electrically isolate said biopotential sensing section from said processing section and including test signal conversion means to convert digital test signals from said analog to digital converter to test optical signals and reconvert said test optical signals to electrical digital test signals at said processing section and control conversion means to convert said control signals from said processing section to optical control signals and reconvert said optical control signals to electrical signals at said biopotential sensing section.

7. An apparatus for sensing a condition at a test site on a human or animal subject by detecting DC biopotentials during a test period at the test site, said apparatus being powered by an AC power supply having an AC line frequency and comprising:

a biopotential sensing section including at least one DC biopotential reference sensor for contacting the subject at a reference location, a plurality of DC biopotential test sensors for contacting the subject at spaced locations at the test site, each said test sensor operating with a reference sensor to detect DC biopotentials which are present at said test site and to provide DC test potentials as a function thereof, and an analog to digital converter connected to said test sensors for receiving said analog DC test potentials and for performing conversion operations for converting said DC test potentials to digital test signals, a processing section connected to said AC power supply and including a digital processor operative during a test period to sample digital test signals which are a function of a plurality of DC test potentials from each test sensor and to identify potential relationships therebetween, said processor operating to provide control signals to said biopotential sensing section during said test period, and operating to sense said AC line frequency and synchronize the conversion operations of said analog to digital converter with said AC line frequency, and an isolation circuit connected between said biopotential sensing section and said processing section to transmit control signals to said biopotential sensing section and digital test signals to said processing section, said isolation circuit operating to electrically isolate said biopotential sensing section from said processing section.

8. An apparatus for sensing a condition at a test site on a human or animal subject by detecting DC biopotentials during a test period, said apparatus being powered by an AC power supply having an AC line frequency and comprising:

at least one DC biopotential reference sensor for contacting the subject at a reference location, a plurality of DC biopotential test sensors for contacting the subject at spaced locations at the test site, each said test sensor having a signal output and operating with a reference sensor to detect DC biopotentials which are present in the area of said test site and to provide DC test potentials as a function thereof, an analog to digital converter connected to said test sensors for converting DC test potentials to digital test signals, a multiplexor connected between said test sensors and said analog to digital converter for sequentially switching among said test sensors during a test period and performing a parallel to serial conversion, a de-multiplexor connected to the output of said analog to digital converter for decommutating said digital test signals and performing a serial to parallel conversion, and a plurality of separate digital filters connected to said de-multiplexor for receiving said digital test signals from said analog to digital converter, said de-multiplexor providing digital test signals from each of said test sensors to one of said plurality of separate digital filters dedicated to receiving digital test signals from DC test potentials received from only that test sensor.

9. The apparatus of claim 8 which includes a signal ranging circuit connected to said digital filters for passing test signals within a predetermined millivolt range and rejecting test signals outside such predetermined range.

10. The apparatus of claim 8 which includes at least first and second separate sensor arrays, each of said sensor arrays including a plurality of said DC biopotential test sensors, said multiplexer operating during a test period to simultaneously provide DC test potentials from individual test sensors in said first and second sensor arrays, at least one analog to digital converter for each sensor array, each analog to digital converter operating during a test period to receive DC test potentials from its associated sensor array.

11. The apparatus of claim 8 which includes a digital processor operating during a test period to sample a plurality of said digital test signals which are a function of a plurality of DC test potentials from each test sensor, said processor including said digital filters and operating to demultiplex the serial test signals from the analog to digital converter and connect the decommutated digital test signals to said separate digital filters.

12. The apparatus of claim 11 wherein said digital processor senses said AC line frequency and synchronizes the conversion operations of said analog to digital converters with said AC line frequency.

13. An apparatus for sensing a condition at a test site on a human or animal subject by detecting DC biopotentials during a test period which are a function of the electromagnetic field present in the subject at the test site comprising:

a biopotential section including at least one reference electrode for contacting the subject at a reference location and a plurality of test electrodes for contacting the subject at spaced locations in the area of the test site, each test electrode having a signal output and operating with a reference electrode to detect DC biopotentials which are present at the test site and to provide DC test potentials as a function thereof, an analog to digital converter for converting said analog DC test potentials to digital test signals, and a multiplexer connected between said test electrodes and said analog to digital converter for providing serial analog DC test potentials to said analog to digital converter by switching between individual test electrodes during a test period and a processing section including a digital processor operating during a test period to sample and process only digital test signals which are within a range of from −30 mv to +100 mv and to identify potential relationships therebetween while rejecting other test signals.

14. The apparatus of claim 13 wherein said biopotential sensing section includes at least first and second separate electrode arrays, each of said electrode arrays including a plurality of test electrodes, said multiplexer operating during a test period to simultaneously provide DC test potentials from individual test electrodes in said first and second electrode arrays, at least one analog to digital converter for each electrode array, each analog to digital converter operating during a test period to receive DC test potentials from its associated electrode array.

15. The apparatus of claim 14 wherein said processor provides control signals to said biopotential sensing section during said test period, said apparatus including an isolation circuit connected between said biopotential sensing section and said processing section to transmit control signals to said biopotential sensing section and digital test signals to said processing section, said isolation circuit operating to electrically isolate said biopotential sensing section from said processing section.

16. The apparatus of claim 15 wherein said isolation circuit (1) converts digital test signals from said analog to digital converter to optical signals and reconverts said digital test signals to electrical signals at said processing section and (2) converts said control signals from said processing section to optical signals and reconverts said control signals to electrical signals at said biopotential sensing section.

17. The apparatus of claim 16 wherein said processing section is connected to an AC power supply having an AC line frequency.

18. The apparatus of claim 17 wherein said processor senses said AC line frequency and synchronizes the conversion operations of said analog to digital converter with said AC line frequency.

19. The apparatus of claim 18 wherein said processing section includes a de-multiplexer for decommutating the serial digital test signals received from said analog to digital converter for performing a serial parallel conversion and separate digital filters being connected to the separate parallel outputs from said de-multiplexer for filtering said individual digital test signals.

20. A method for sensing and processing DC biopotentials from one or more test sites on a human or animal subject as a function of DC biopotentials present at the test site by using a plurality of spaced DC biopotential sensors in contact with the skin surface of the subject to take DC biopotential measurements, said DC biopotential sensors including one or more DC biopotential reference sensors and a plurality of DC biopotential test sensors which includes:

selecting during a test period a plurality of first and second pairs of DC biopotential sensors from said plurality of spaced DC biopotential sensors, each said first and second selected pair of DC biopotential sensors including a reference and a test sensor, during a test period, taking a plurality of DC biopotential measurements with each said first and second pair of DC biopotential sensors to obtain a plurality of individual DC biopotential test values for each said first pair of DC biopotential sensors and a plurality of individual DC biopotential test values for each said second pair of DC biopotential sensors in each of said plurality of selected first and second pairs of DC biopotential sensors, comparing each DC biopotential test value obtained by a first of each said selected first and second pairs of DC biopotential sensors with a DC biopotential test value obtained by a second of each said selected first and second pairs of DC biopotential sensors to obtain a difference value therebetween and to thereby obtain a plurality of difference values for each selected first and second pair of DC biopotential sensors, and at the end of the test period averaging the plurality of differential values for each selected first and second pair of DC biopotential sensors to obtain a single average differential value for each selected first and second pair of DC biopotential sensors.

21. The method of claim 20 which includes comparing the single average differential values for all of said selected pairs of first and second DC biopotential sensors to identify the highest and the lowest single average differential value for the test period and obtaining maximum differential value for the test period indicative of the difference between the highest and lowest single average differential values.

22. A method for simulating the DC biopotentials for points of a test area on a human or animal subject which are not directly contacted by DC biopotential sensors applied to the skin surface of subject in the test area which includes:

applying one or more DC biopotential reference sensors to the subject, applying a plurality of spaced DC biopotential test sensors to the skin surface of the subject in the test area with each test sensor at a known separate one of a plurality of measurement points, taking a plurality of DC biopotential measurements with a reference DC biopotential sensor and each of the DC biopotential sensors at each measurement point during a test period to obtain a plurality of DC biopotential test values for each measurement point, averaging the DC biopotential test values for each measurement point to obtain an average DC biopotential value for each measurement point, and inferring a DC biopotential value for an interpolation point in the test area not contacted by a DC biopotential test sensor by vector summing wherein the sum of the average DC biopotential values for the measurement points relative to the vector distance from the interpolated point to each measurement point is used to infer said interpolation point DC biopotential value.

23. The method of claim 22 which includes inferring a DC biopotential value for a plurality of interpolation points and subsequently generating an image using the average DC biopotential values for each measurement point and the DC biopotential inferred for each interpolation point.

* * * * *